(12) United States Patent
Obata et al.

(10) Patent No.: US 11,033,176 B2
(45) Date of Patent: Jun. 15, 2021

(54) MEDICAL SYSTEM, MEDICAL DEVICE, AND MEDICAL METHOD

(71) Applicant: SONY CORPORATION, Tokyo (JP)

(72) Inventors: Koji Obata, Tokyo (JP); Makoto Korehisa, Kanagawa (JP); Kazumi Sato, Kanagawa (JP); Kan Iibuchi, Kanagawa (JP); Kazunori Yamamoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 318 days.

(21) Appl. No.: 15/735,331

(22) PCT Filed: Jul. 11, 2016

(86) PCT No.: PCT/JP2016/070431
§ 371 (c)(1),
(2) Date: Dec. 11, 2017

(87) PCT Pub. No.: WO2017/018187
PCT Pub. Date: Feb. 2, 2017

(65) Prior Publication Data
US 2018/0168434 A1 Jun. 21, 2018

(30) Foreign Application Priority Data
Jul. 24, 2015 (JP) .............................. JP2015-146361

(51) Int. Cl.
*G06F 1/24* (2006.01)
*G06F 9/00* (2006.01)
*A61B 1/00* (2006.01)
(Continued)

(52) U.S. Cl.
CPC ...... *A61B 1/00025* (2013.01); *A61B 1/00048* (2013.01); *A61B 1/05* (2013.01);
(Continued)

(58) Field of Classification Search
CPC .................................................. A61B 1/00025
See application file for complete search history.

(56) References Cited

U.S. PATENT DOCUMENTS 5,269,022 A 12/1993 Shinjo et al.
6,527,719 B1 * 3/2003 Olsson .................. G06F 1/3206
713/323
(Continued)

FOREIGN PATENT DOCUMENTS

JP 3-278126 A 12/1991
JP 2002-209876 A 7/2002
(Continued)

OTHER PUBLICATIONS

International Search Report dated Sep. 20, 2016 in PCT/JP2016/070431.

*Primary Examiner* — Mohammed H Rehman
(74) *Attorney, Agent, or Firm* — Xsensus, LLP

(57) ABSTRACT

The present disclosure relates to a surgical system, a surgical device, and a surgical method with which startup time can be shortened.
Upon receipt of an instruction from a startup execution process, a high-speed startup driver creates a high-speed startup image and writes it to an SSD. The startup execution process is a process that is executed first after an OS is started up, and has the function of executing, in cooperation with the high-speed startup driver, startup of various processes in an endoscope program, creation of a high-speed startup image, and return from the high-speed startup image. The present disclosure can be applied to, for example, a surgical system provided with an imaging device including an endoscope or a microscope.

13 Claims, 9 Drawing Sheets

(51) Int. Cl.
*A61B 90/00* (2016.01)
*G06F 9/445* (2018.01)
*G06F 9/4401* (2018.01)
*A61B 1/05* (2006.01)
*A61B 5/00* (2006.01)

(52) U.S. Cl.
CPC .............. *A61B 90/00* (2016.02); *G06F 9/445* (2013.01); *G06F 9/4406* (2013.01); *A61B 1/00016* (2013.01); *A61B 5/7232* (2013.01)

(56) References Cited

U.S. PATENT DOCUMENTS

| | | | | |
|---|---|---|---|---|
| 8,583,244 | B1* | 11/2013 | Calle | A61N 1/36036 |
| | | | | 607/137 |
| 2002/0175992 | A1* | 11/2002 | Eino | A61B 1/00048 |
| | | | | 348/65 |
| 2004/0076259 | A1 | 4/2004 | Jensen et al. | |
| 2005/0216552 | A1* | 9/2005 | Fineberg | G06F 12/0284 |
| | | | | 709/203 |
| 2005/0235094 | A1* | 10/2005 | Sawada | G06F 9/5016 |
| | | | | 711/1 |
| 2006/0059380 | A1* | 3/2006 | Kimura | G06F 1/3296 |
| | | | | 713/323 |
| 2007/0161861 | A1* | 7/2007 | Kawai | A61B 1/00055 |
| | | | | 600/145 |
| 2008/0167736 | A1 | 7/2008 | Swayze et al. | |
| 2010/0149844 | A1* | 6/2010 | Yasuda | H02M 1/36 |
| | | | | 363/95 |
| 2010/0223452 | A1* | 9/2010 | Chung | G06F 9/441 |
| | | | | 713/2 |
| 2011/0270179 | A1* | 11/2011 | Ouyang | A61B 1/00062 |
| | | | | 604/110 |
| 2013/0073813 | A1* | 3/2013 | Bacik | G06F 12/0866 |
| | | | | 711/144 |
| 2014/0067889 | A1* | 3/2014 | Mortensen | G06F 7/57 |
| | | | | 708/201 |
| 2014/0122854 | A1 | 5/2014 | Kato | |

FOREIGN PATENT DOCUMENTS

| | | |
|---|---|---|
| JP | 2002-345745 A | 12/2002 |
| JP | 2008-246188 A | 10/2008 |
| JP | 2014-85909 A | 5/2014 |
| WO | WO 2014/069276 A1 | 5/2014 |

* cited by examiner

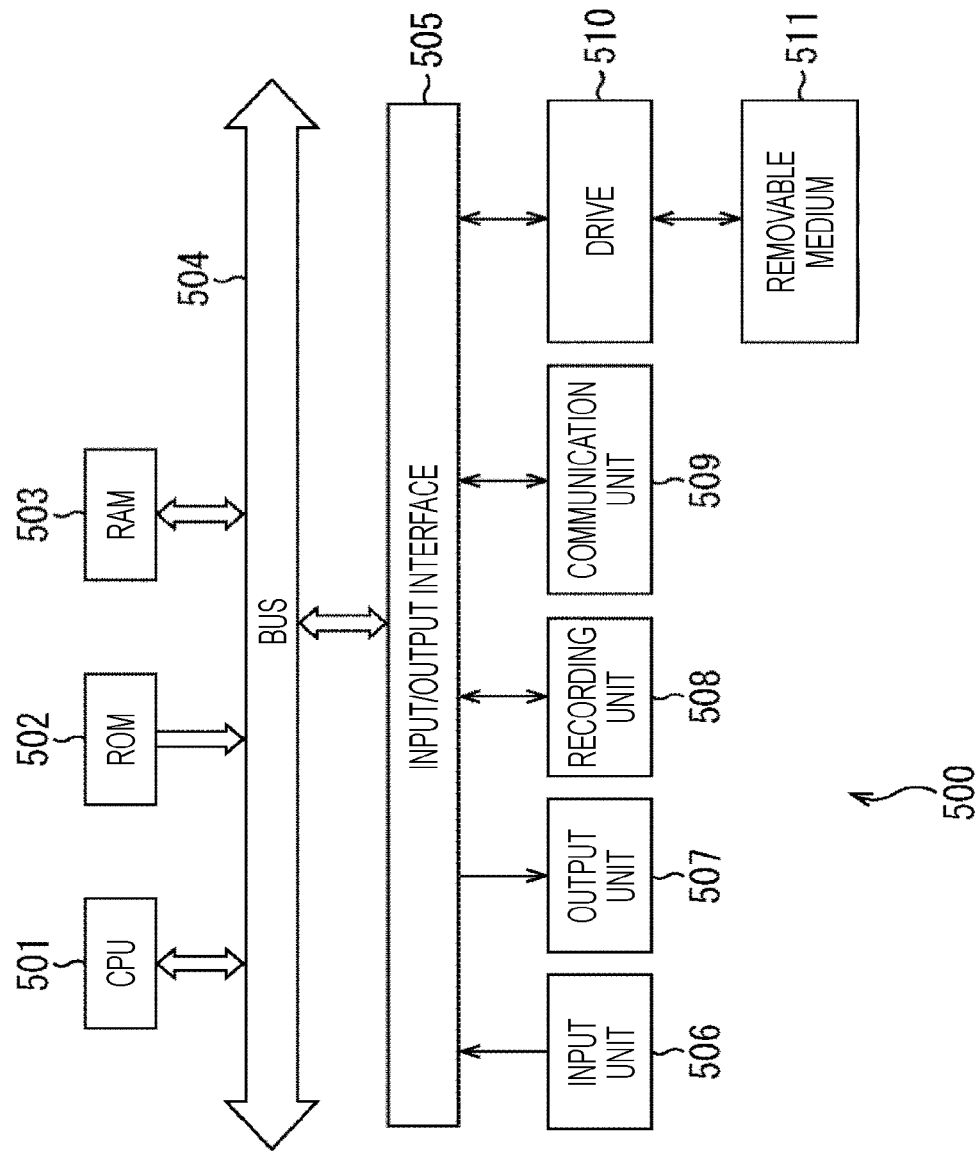

MEDICAL SYSTEM, MEDICAL DEVICE, AND MEDICAL METHOD

TECHNICAL FIELD

The present disclosure relates to a surgical system, a surgical device, and a surgical method, and in particular to a surgical system, a surgical device, and a surgical method with which startup time can be shortened.

BACKGROUND ART

Patent Document 1 discloses that an endoscope system can be constructed at low cost using a personal computer. In such an endoscope system, a general-purpose OS is adopted as an operating system, and no consideration is given to startup subsequent to power-on. In addition, due to recent improvements in the functionality of the operating system, it takes several tens of seconds to start up the operating system.

CITATION LIST

Patent Document

Patent Document 1: Japanese Patent Application Laid-Open No. 2002-345745

SUMMARY OF THE INVENTION

Problems to be Solved by the Invention

Fast startup is one of the important capabilities of medical devices for use in surgery such as an endoscope. For example, it is desirable that medical devices that may encounter every-second-counts situations such as emergency surgery and return from unintended power-off during surgery be able to be started up at high speed.

In addition, even medical devices have become more and more advanced in recent years, and startup time has increased accordingly. For example, medical devices are connected to hospital and external networks to exchange various types of information, and operate in cooperation with mobile devices.

The present disclosure has been made in consideration of the above-mentioned circumstances, so that startup time can be shortened.

Solutions to Problems

A surgical system according to an aspect of the present technology includes: a surgical imaging device that captures an image for surgery; and a surgical device including: an image processing unit that processes the image captured by the surgical imaging device; and a loading unit that reads, at time of startup, information of a program space on a memory recorded in a recording medium after startup of an operating system (OS) is finished, and loads the information of the program space on the memory.

The memory includes a double-data-rate (DDR) RAM.

The recording medium includes a solid state drive (SSD).

A recording unit that records the information of the program space in the recording medium after the startup of the OS is finished can further be provided.

After the startup of the OS is finished, the recording unit can start up processes of a surgical application program, collaborate with a predetermined process of the processes, cause each process to reserve a resource and to execute sleep, and record the information of the program space.

Order of starting up the surgical application program is order of proximity to hardware.

The surgical application program is an endoscopic surgical application program.

The surgical imaging device is an endoscope.

The surgical application program is a microscopic surgical application program.

The surgical imaging device is a surgical microscope.

The recording medium has a startup mode area indicating a startup mode, the predetermined process changes a recording mode of the startup mode area of the recording medium to a high-speed startup mode when the information of the program space is recorded, and in a case where the recording mode of the startup mode area of the recording medium is the high-speed startup mode, the loading unit can read the information of the program space recorded in the recording medium, and load the information of the program space on the memory.

In a surgical method according to an aspect of the present technology, a surgical device reads, at time of startup, information of a program space on a memory recorded in a recording medium after startup of an operating system (OS) is finished, and loads the information of the program space on the memory.

A surgical device according to an aspect of the present technology includes a loading unit that reads, at time of startup, information of a program space on a memory recorded in a recording medium after startup of an operating system (OS) is finished, and loads the information of the program space on the memory.

According to an aspect of the present technology, at time of startup, information of a program space on a memory recorded in a recording medium after startup of an operating system (OS) is finished is read and loaded on the memory.

Effects of the Invention

According to the present technology, it is possible to shorten startup time.

Note that the effects described in the present specification are merely examples, and the effects of the present technology are not limited to the effects described in the present specification. Any additional effect may also be obtained.

BRIEF DESCRIPTION OF DRAWINGS

FIG. 9 is a block diagram illustrating an exemplary configuration of a personal computer to which the present technology is applied.

MODE FOR CARRYING OUT THE INVENTION

Hereinafter, modes for carrying out the present disclosure (hereinafter referred to as "embodiments") will be described. Note that the description will be provided in the following order.
1. First Embodiment
2. Second Embodiment 1. First Embodiment

[Exemplary Overall Configuration of Endoscope System]

Figure 1:
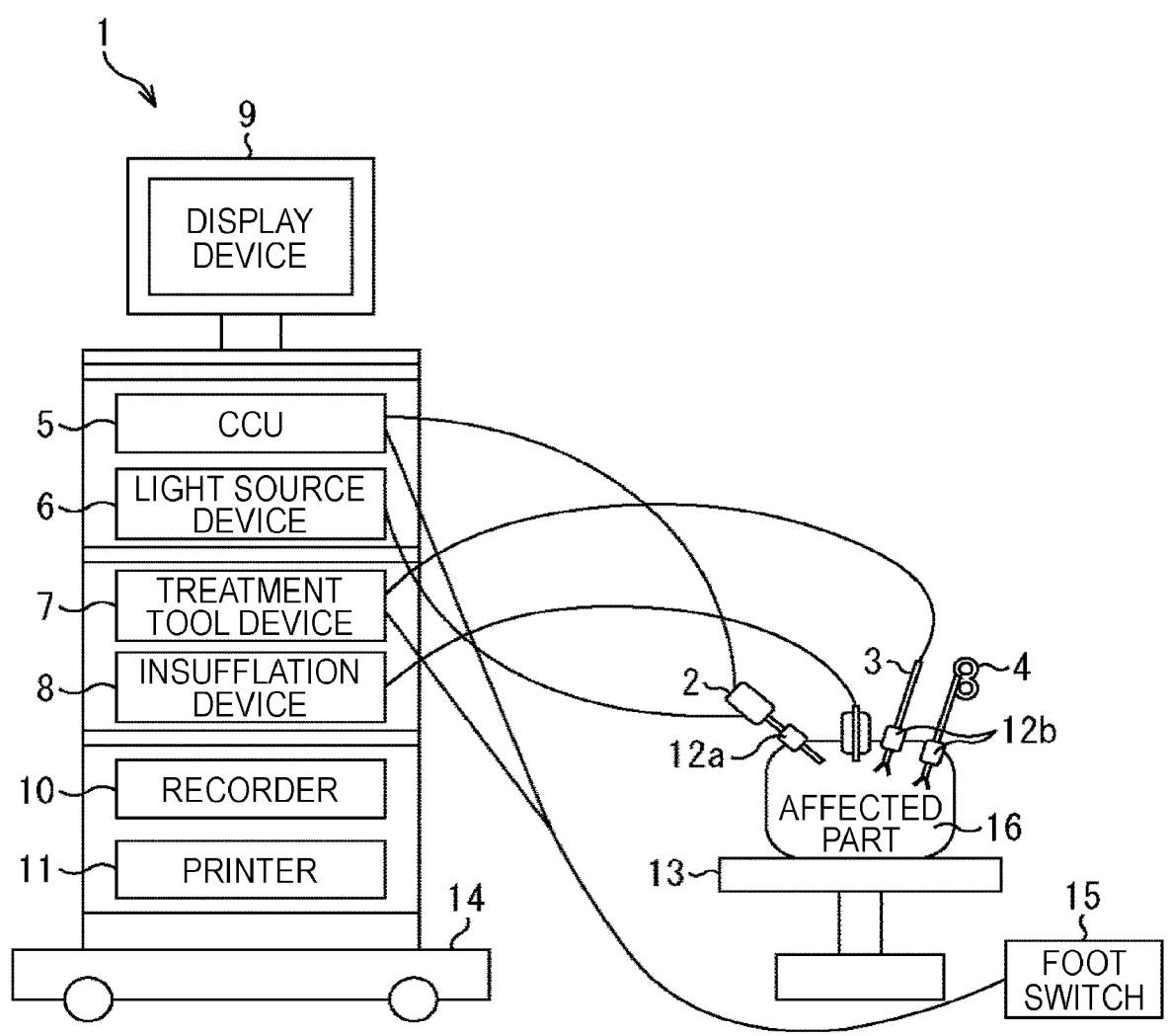
FIG. 1 is a block diagram illustrating an exemplary overall configuration of a system for endoscopic surgery to which the present technology is applied.

FIG. 1 is a diagram illustrating an exemplary overall configuration of a system for endoscopic surgery as a surgical system of the present technology.

In recent years, endoscopic surgery has been performed in the medical field instead of conventional laparotomy surgery. For example, in a case where abdominal surgery is performed, a system for endoscopic surgery 1 arranged in an operating room as illustrated in FIG. 1 is used. Instead of cutting the abdominal wall and opening the abdomen as in the past, opening tools called trocars 12a, 12b are attached to the abdominal wall at several places, and a camera head unit of a laparoscope (endoscope) (hereinafter simply referred to as a camera head unit) 2, an energy treatment tool 3, forceps 4, and the like are inserted into the body through the holes provided in the trocars 12a, 12b. Then, while looking at video images of an affected part (tumor or the like) 16 captured by the camera head unit 2 in real time, treatment such as excision of the affected part 16 with the energy treatment tool 3 or the like is performed. The camera head unit 2, the energy treatment tool 3, and the forceps 4 are held by a surgeon, an assistant, a scopist, a robot, or the like.

In an operating room in which such endoscopic surgery is performed, a cart 14 equipped with devices for endoscopic surgery, a patient bed 13 on which a patient lies, a foot switch 15, and the like are arranged. The cart 14 is equipped with devices, as medical devices, such as a camera control unit (CCU) 5, a light source device 6, a treatment tool device 7, an insufflation device 8, a display device 9, a recorder 10, and a printer 11, for example.

An image signal of the affected part 16 captured through an observation optical system of the camera head unit 2 is transmitted to the CCU 5 via a camera cable, and subjected to signal processing in the CCU 5. After that, the image signal is output to the display device 9, on which an endoscope image of the affected part 16 is displayed. The CCU 5 may be wirelessly connected to the endoscope 2 instead of being coupled via the camera cable.

The light source device 6 is coupled to the camera head unit 2 via a light guide cable, and can irradiate the affected part 16 with beams of light of various wavelengths in a switching manner. The treatment tool device 7 is a high-frequency output device that outputs a high-frequency current to the energy treatment tool 3 that cuts the affected part 16 using electric heat, for example.

The insufflation device 8 is provided with an air supply/suction means to send air, for example, to an abdominal region in the patient's body. The foot switch 15 is adapted to control the CCU 5, the treatment tool device 7, and the like in response to a trigger signal, i.e., foot operation by a surgeon, an assistant, or the like.

Figure 2:
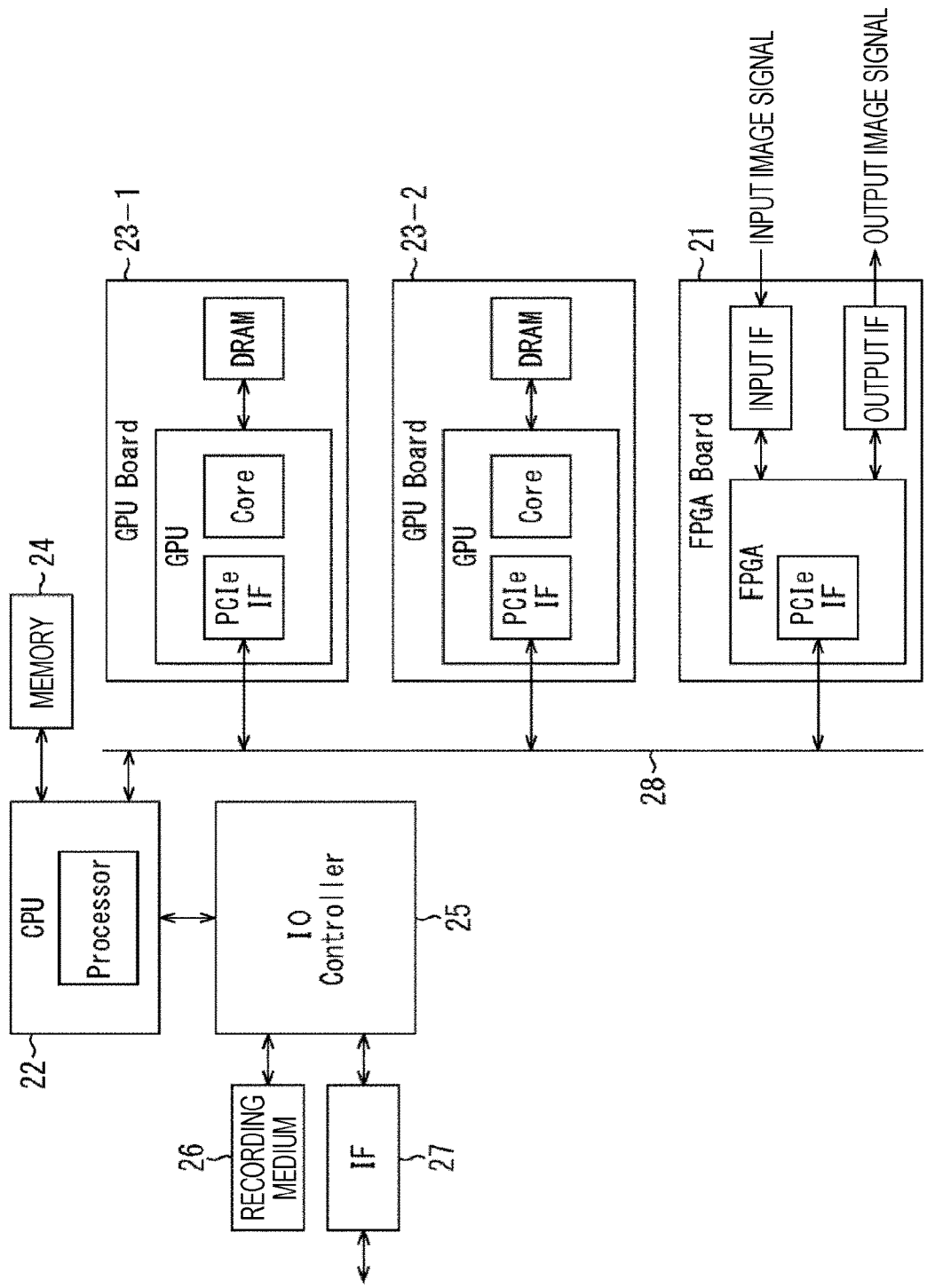
FIG. 2 is a diagram illustrating an example of a hardware configuration of a CCU of FIG. 1.

FIG. 2 is an explanatory diagram illustrating an example of a hardware configuration of the CCU 5 of FIG. 1. The CCU 5 includes, for example, an FPGA board 21, a CPU 22, GPU boards 23-1, 23-2, a memory 24, an IO controller 25, a recording medium. 26, and an interface 27. Further, the FPGA board 21, the CPU 22, and the GPU boards 23-1, 23-2 are coupled by a bus 28, for example. The FPGA board 21 includes, for example, an FPGA, an input interface to which an input image signal is input from the camera head unit 2 of FIG. 1, and an output interface from which an output image signal is output to the display device 9 of FIG. 1.

The CPU 22 and the GPU boards 23-1, 23-2 perform various types of processing by executing various kinds of software such as related software, for example. The CPU 22 includes a processor. Each of the GPU boards 23-1, 23-2 includes a graphics processing unit (GPU) and a dynamic random access memory (DRAM).

In the memory 24, for example, various kinds of data such as data corresponding to an input image signal from the camera head unit 2 and data corresponding to an output image signal to the display device 9 are stored. The CPU 22 plays the role of controlling writing and reading of various kinds of data to and from the memory 24.

The CPU 22 divides image data stored in the memory 24 according to the data stored in the memory 24, the processing abilities of the GPU boards 23-1, 23-2, and the processing contents. Then, each GPU of the GPU boards 23-1, 23-2 performs predetermined processing on the divided and supplied data, and outputs the processing result to the CPU 22.

The IO controller 25 plays the role of, for example, controlling the transmission of signals between the CPU 22, the recording medium 26, and the interface 27.

The recording medium 26 functions as a storage unit (not illustrated), and stores various kinds of data such as image data and various applications. Here, the recording medium 26 is exemplified, for example, by a solid state drive (SSD) or the like. Further, the recording medium 26 may be detachable from the CCU 5.

Examples of the interface 27 include a universal serial bus (USB) terminal associated with a processing circuit, a local area network (LAN) terminal associated with a transmission/reception circuit, and the like.

Note that the hardware configuration of the CCU 5 is not limited to the configuration illustrated in FIG. 2. For example, although the two GPU boards 23-1, 23-2 are illustrated in the example of FIG. 2, two or more GPU boards may be used. Further, in a case where the CPU 22 has the function of the GPU, the CCU 5 does not have to include the GPU boards 23-1, 23-2.

Figure 3:
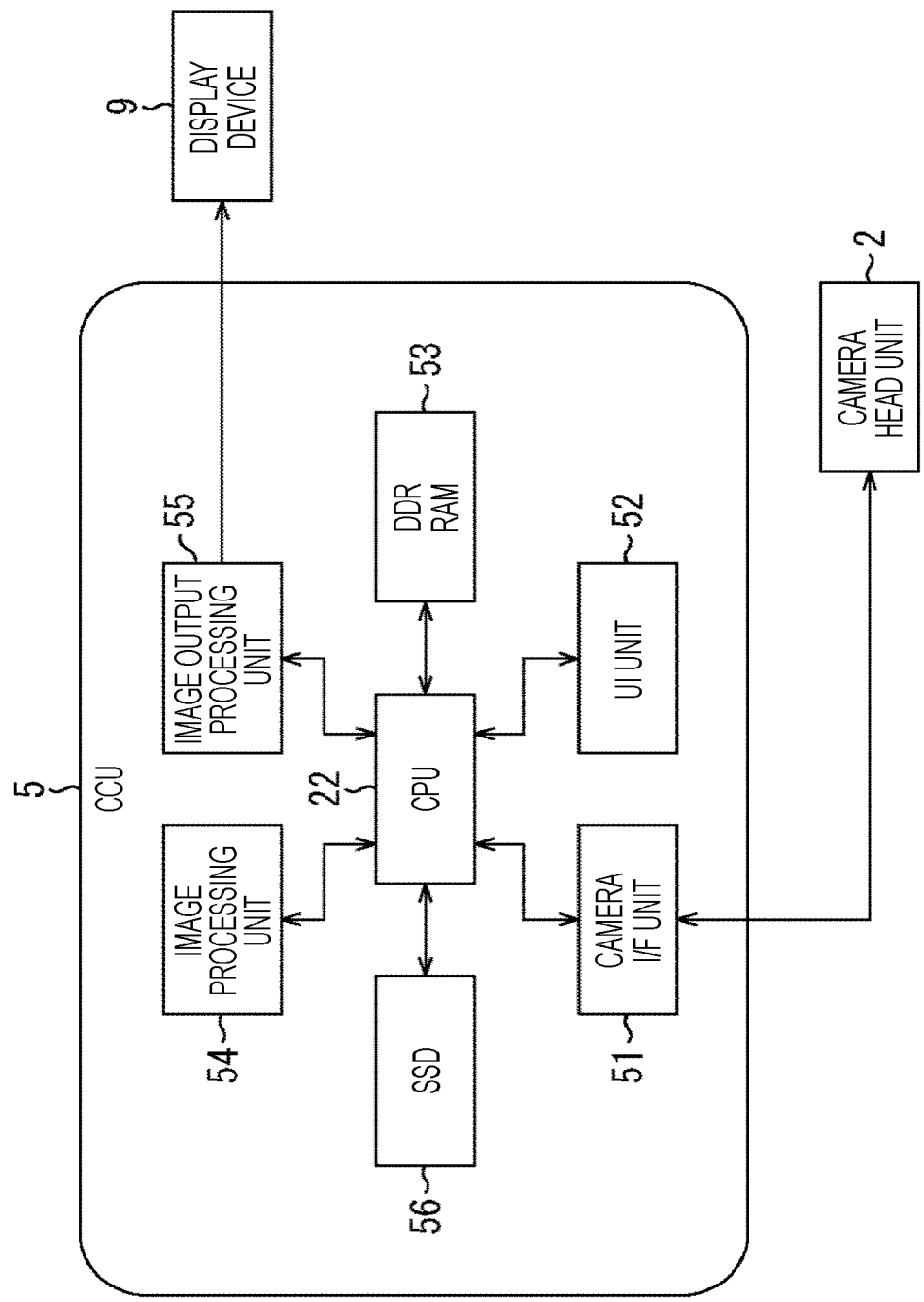
FIG. 3 is a block diagram illustrating an example of an internal configuration of the CCU of FIG. 1.

FIG. 3 is a block diagram illustrating an example of an internal configuration of the CCU 5 of FIG. 1.

The CCU 5 includes the CPU 22, a camera I/F 51, a user interface (UI) unit 52, a DDR RAM 53, an image processing unit 54, an image output processing unit 55, and an SSD 56. The camera I/F unit 51, the user interface (UI) unit 52, the DDR RAM 53, the image processing unit 54, the image output processing unit 55, and the solid state drive (SSD) 56 are mutually connected to the CPU 22 to exchange image data and the like via the CPU 22.

Note that the RAM is exemplified by, but not limited to, the DDR RAM, and another RAM may be used. Similarly, the SSD 56 may be a secondary storage device other than the SSD, e.g., a hard disk and a ROM area. However, since the operating speed of such a device also affects the startup time of the system, careful selection is required.

The camera I/F unit 51 receives endoscope images captured by the camera head unit 2 via an optical fiber or the like, and stores the endoscopic images in the DDR RAM 53. The UI unit 52 inputs information corresponding to the operation by a user through a button, an operation panel, or the like, and supplies the information to the CPU 22. The DDR RAM 53 stores endoscope images from the camera I/F unit 51, image data processed by the image processing unit 54, and the like.

The image processing unit 54 corresponds to the GPU boards 23-1, 23-2 in FIG. 2. The image processing unit 54 reads image data from the DDR RAM 53, performs development processing and image quality improvement processing, and saves the processed image data in the DDR RAM 53 again.

The image output processing unit 55 reads the image data processed by the image processing unit 54 from the DDR RAM 53, adjusts the output image size and the like, and outputs the adjusted image data to the display device 9. Correspondingly, the display device 9 displays the endoscope image corresponding to the adjusted image data.

The CPU 22 communicates with the camera head unit 2 via the camera I/F 51, and notifies the camera head unit 2 of setting information such as a shutter speed input by the user operating the endoscope through the UI unit 52. Further, the CPU 22 acquires detection information from the image processing unit 54, and notifies the camera head unit 2 of various control values such as an exposure control value via the camera I/F 51.

Figure 4:
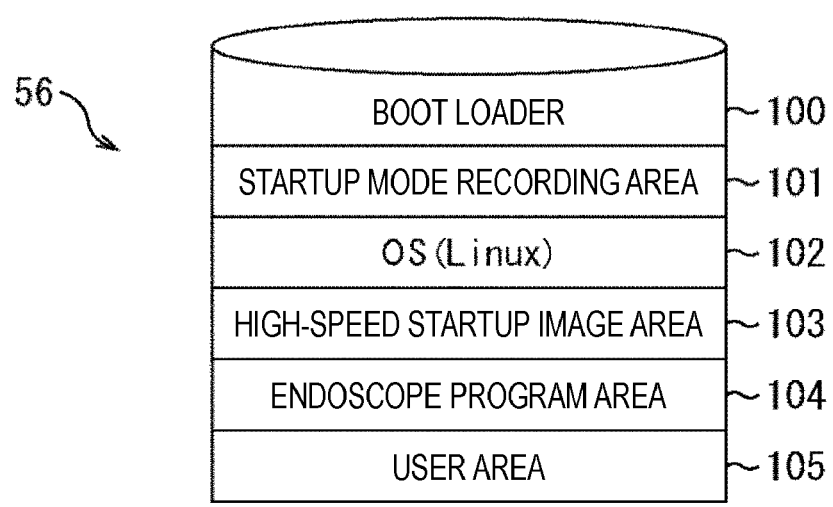
FIG. 4 is a diagram illustrating an exemplary partition configuration of the inside of an SSD of FIG. 3.

FIG. 4 is a diagram illustrating an exemplary partition configuration of the inside of the SSD 56 of FIG. 3.

The SSD 56 is partitioned into a boot loader 100, a startup mode recording area 101, an OS (Linux (registered trademark)) 102, a high-speed startup image area 103, an endoscope program area 104, and a user area 105. In addition, program codes, data and the like corresponding to the area are recorded in each area.

Note that data and the like corresponding to an application in an endoscope program are recorded in the user area 105. At the time of startup, the boot loader 100 is first read. The boot loader 100 determines whether to execute the OS 102 or the high-speed startup image area 103 according to the contents recorded in the startup mode recording area 101, and performs execution.

The OS 102 is not limited to Linux (registered trademark), and another OS may be used.

Figure 5:
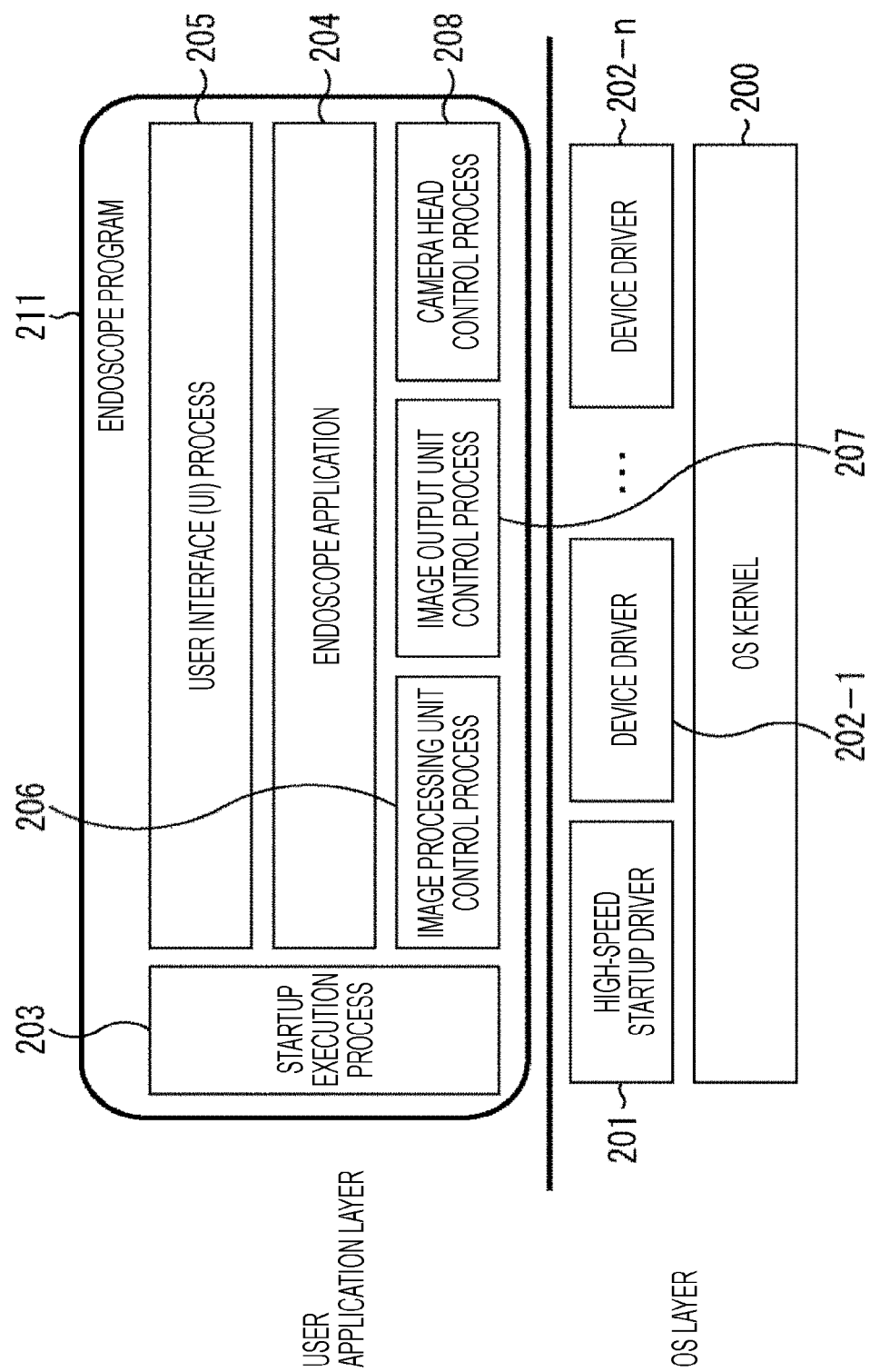
FIG. 5 is a diagram illustrating an exemplary software configuration of the CCU of FIG. 1.

FIG. 5 is a diagram illustrating an exemplary software configuration of the CCU 5 of the present technology.

The software of the CCU 5 is roughly divided into an OS layer and a user application layer. In the OS layer, an OS kernel 200, a high-speed startup driver 201, various device drivers 202-1 to 202-n, and the like are executed.

In the user application layer, a startup execution process 203, an endoscope application 204, a user interface (UI) process 205, an image processing unit control process 206, an image output control process 207, and a camera head control process 208 are executed as an endoscope program 211.

Specifically, upon receipt of an instruction from the startup execution process 203, the high-speed startup driver 201 creates a high-speed startup image and writes it to the SSD 56. The startup execution process 203 is a process that is executed first after the OS is started up, and has the function of executing, in cooperation with (in collaboration with) the high-speed startup driver 201, startup of various processes in the endoscope program 211, creation of a high-speed startup image, and return from the high-speed startup image created at the time of initial startup. The startup execution process 203 knows the order of starting up the processes other than the startup execution process 203 of the endoscope program 211, and executes these processes in this order. In the endoscope program 211, the processes other than the startup execution process 203 are executed in order from the bottom since the proximity of control to hardware is higher in the lower parts of the drawing.

The user interface process 205 has the function of executing input from the user and output to the user, and instructs the endoscope application 204 to execute a function or change the setting according to the input from the user. The user interface process 205 also has the role of receiving the execution results for instructions and the like from the endoscope application 204 and presenting the execution results to the user.

The endoscope application 204 receives instructions and settings from the user, and requests the image processing unit control process 206, the image output unit control process 207, and the camera head control process 208 to execute necessary operations. For example, the endoscope application 204 requests the image output unit control process 207 to execute operations related to the change of output resolution, requests the image processing unit control process 206 to execute operations related to emphasizing processing on the image, and requests the camera head control process 208 to execute operations related to a speed request for an electronic shutter.

Figure 6:
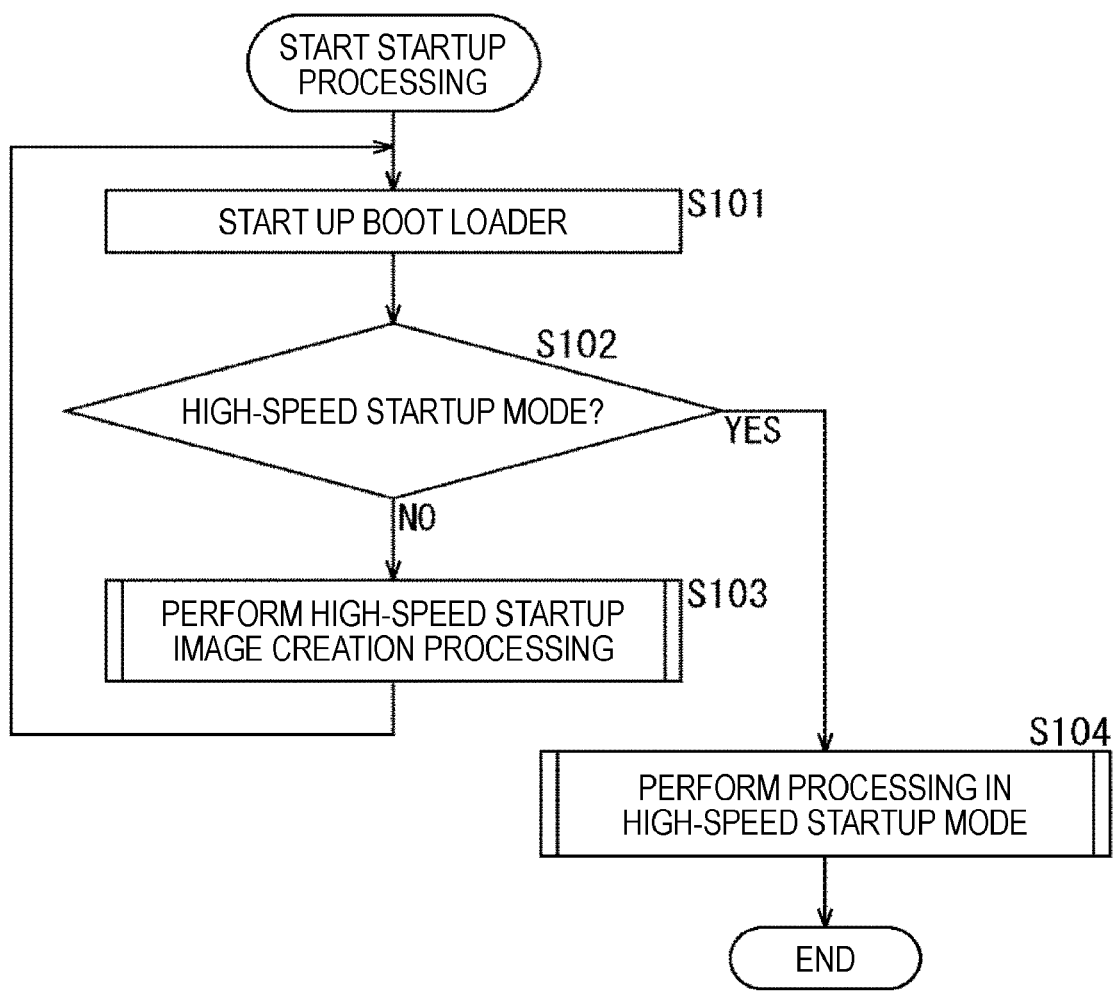
FIG. 6 is a flowchart for explaining startup processing for the CCU of FIG. 1.

Next, startup processing for the CCU 5 will be described with reference to a flowchart of FIG. 6.

In step S101, the boot loader 100 is started up by a startup instruction from the user, and the boot loader 100 reads the startup mode recording area 101 recorded in the SSD 56.

In step S102, the boot loader 100 determines whether a high-speed startup mode is set. If the startup mode recording area 101 has not been changed to the high-speed startup mode, the processing proceeds to step S103.

In step S103, the boot loader 100 executes high-speed startup image creation processing. In the high-speed startup image creation processing in step S103, as will be described later with reference to FIG. 7, a high-speed startup image is created, the created high-speed startup image is written to the high-speed startup image area 103 of the SSD 56, and the startup mode of the startup mode recording area 101 is changed to the high-speed startup mode. Then, the processing returns to step S101, and the subsequent processing is repeated.

On the other hand, in a case where the startup mode recording area 101 has been changed to the high-speed startup mode, it is determined in step S102 that the high-speed startup mode is set, and the processing proceeds to step S104.

In step S104, the boot loader 100 executes processing in the high-speed startup mode. In the processing in the high-speed startup mode in step S104, as will be described later with reference to FIG. 8, the high-speed startup image written in step S103 is read from the high-speed startup image area 103 of the SSD 56, sleep of each process is canceled by the high-speed startup driver 201, various programs of the endoscope program 211 are notified to cancel sleep, the startup is completed, and the CCU 5 is put into a usable state.

Figure 7:
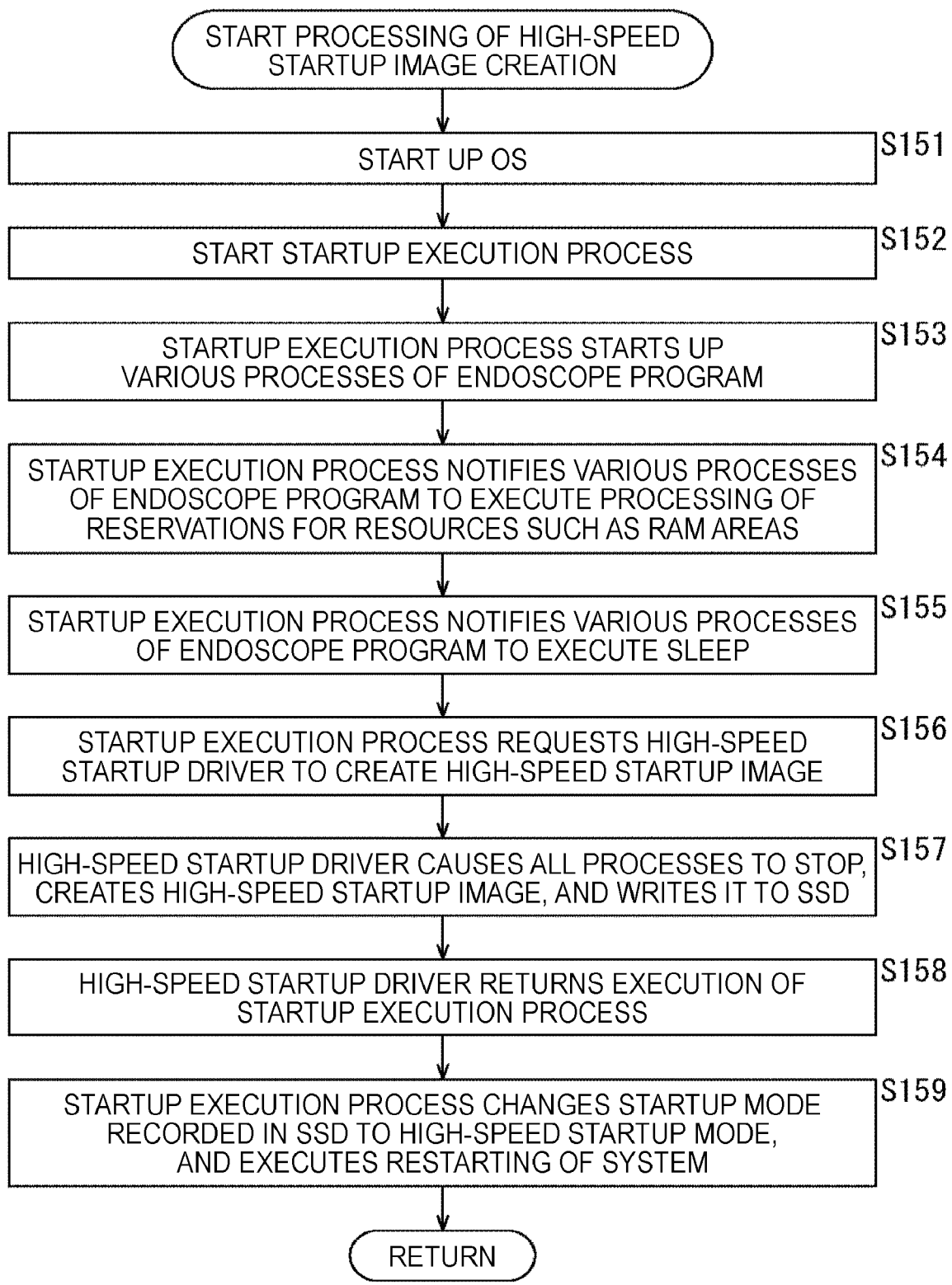
FIG. 7 is a flowchart for explaining high-speed startup image creation processing in step S103 of FIG. 6.

Next, the high-speed startup image creation processing in step S103 of FIG. 6 will be described with reference to the flowchart of FIG. 7.

In step S151, the boot loader 100 starts up the OS 102 by loading the OS 102 in the SSD 56 on the DDR RAM 53. Initialization of the memory and initialization of various kinds of hardware are performed by the OS 102. Once the execution of the user process is enabled, the OS kernel 200 starts the startup execution process 203 in step S152.

In step S153, the startup execution process 203 starts up various processes of the endoscope program 211. The various processes do not function until notified by the startup execution process 203.

After all the processes are started up, in step S154, the startup execution process 203 notifies the various processes of the endoscope program 211 to execute, for example, reservations for resources such as RAM areas. Correspondingly, the various processes execute reservations for resources.

In step S155, the startup execution process 203 notifies each process of the endoscope program 211 to execute sleep. After each process is put into sleep, in step S156, the startup execution process 203 requests the high-speed startup driver 201 to create a high-speed startup image.

In step S157, the high-speed startup driver 201 puts all the processes including the unsleeping startup execution process into sleep, and sets a program space on the DDR RAM 53 such that it is not changed. After that, the high-speed startup driver 201 starts creating the high-speed startup image, and writes, to the high-speed startup image area 103 of the SSD 56, the contents of the program space on the DDR RAM 53 and address information for return. Thus, the high-speed startup image means the contents of the program space on the DDR RAM 53.

After the writing to the SSD 56 is finished, in step S158, the high-speed startup driver 201 cancels the sleep of the startup execution process 203 for return. In step S159, the returned startup execution process 203 changes the startup mode recorded in the SSD 56 to the high-speed startup mode, and executes restarting of the system.

Note that, in practice, this processing is performed on the manufacturing side at the time of shipment, for example. However, at the time of updating the software, the high-speed startup image is updated after the updating. In addition, in a case where the CPU, the RAM, or the like is replaced, it is necessary to recreate the high-speed startup image, and execution is enabled when a serviceman switches the startup mode.

Figure 8:
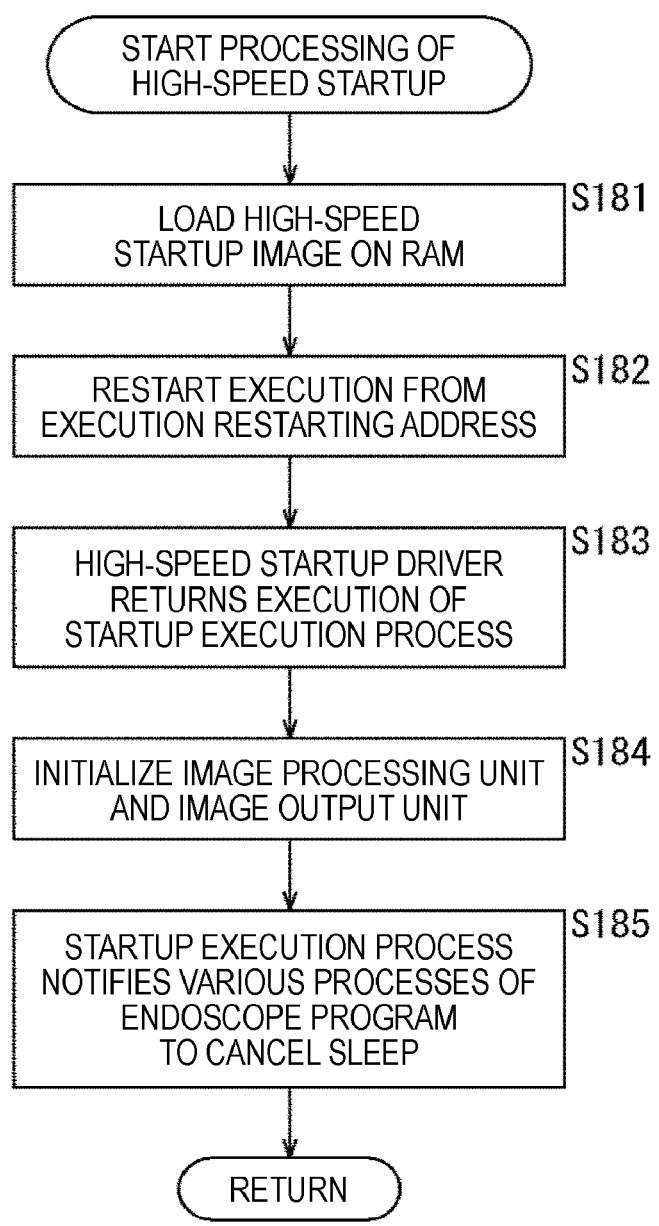
FIG. 8 is a flowchart for explaining processing in a high-speed startup mode in step S104 of FIG. 6.

Next, the processing in the high-speed startup mode in step S104 of FIG. 6 will be described with reference to the flowchart of FIG. 8. In the example of FIG. 8, since the startup mode has been changed to the high-speed startup mode by the time the boot loader 100 reads the startup mode recording area 101, the processing in the high-speed startup mode is executed.

In step S181, the boot loader 100 loads the high-speed startup image recorded in the SSD 56 on the DDR RAM 53. In step S182, the boot loader 100 restarts execution from the recorded return address.

In step S183, the high-speed startup driver 201 cancels the sleep of the startup execution process 203 to return execution. Note that in both steps S183 and S158 of FIG. 7, the high-speed startup driver 201 cancels the sleep of the startup execution process 203 for return. However, the startup execution process 203 is configured to be able to determine, on the basis of information from the high-speed startup driver 201, whether the sleep cancellation is for the high-speed startup or for the creation of a high-speed startup image.

In step S184, the startup execution process 203 subjected to the sleep cancellation performs initialization of the image processing unit 54 and the image output processing unit 56.

In step S185, the startup execution process 203 notifies various programs of the endoscope program 211 to cancel the sleep, and completes the startup. As a result, the CCU is ready for use.

As described above, the state of the program space after the startup of the CCU 5 and the position of the program for return are recorded in the SSD or the like, so that return to the position of the program can be performed at the time of startup. Therefore, the startup time of the endoscope system can be shortened.

In addition, it is possible to reduce the influence of improvements in the functionality on the startup time of the OS.

Note that in the embodiment of the above description, the system for endoscopic surgery has been described as an example of the surgical system to which the present technology is applied. However, the present technology is not limited to the system for endoscopic surgery, and can be applied to any surgical system. For example, the present technology can be applied to a system for microscopic surgery for supporting microscopic surgery which is laparotomy surgery with the use of a microscope. A microscope is used for the system for microscopic surgery in place of the endoscope. The microscope is similar to the endoscope in that it has the camera head unit 2 and is controlled by the CCU 5 to capture a surgical site and an area around the surgical site. In this case, the endoscope application 211 and the endoscope program 211 described above with reference to FIG. 5 serve as a microscope application and a microscope program, respectively.

Therefore, the present technology described above in each embodiment can be applied to such a system for microscopic surgery as in the case of the system for endoscopic surgery, and similar effects can be exhibited.

Further, the present technology can be applied to an image obtained by photographing a subject other than a living body.

Further, the present technology can be applied to any device having a photographing function other than medical devices. Examples of such a device include a digital camera, an in-vehicle image sensor, a monitoring camera for monitoring agricultural crops or for security, an endoscope system for industrial use (fiberscope), and the like.

2. Second Embodiment

[Personal Computer]

The above-mentioned sequence of processes can be executed by hardware, and can also be executed by software. In a case where the sequence of processes is executed by the software, a program constituting the software is installed on a computer. As used herein, the computer includes a computer incorporated in dedicated hardware, a general-purpose personal computer that can install various programs to execute various functions, or the like.

FIG. 9 is a block diagram illustrating an exemplary configuration of hardware of the personal computer that executes the above-mentioned sequence of processes by means of the programs.

In the personal computer 500, a central processing unit (CPU) 501, a read only memory (ROM) 502, and a random access memory (RAM) 503 are coupled to one another by a bus 504.

An input/output interface 505 is further connected to the bus 504. An input unit 506, an output unit 507, a storage unit 508, a communication unit 509, and a drive 510 are connected to the input/output interface 505.

The input unit 506 includes a keyboard, a mouse, a microphone, and the like. The output unit 507 includes a display, a speaker, and the like. The storage unit 508 includes a hard disk, a non-volatile memory, and the like. The communication unit 509 includes a network interface or the like. The drive 510 drives a removable medium 511 such as a magnetic disc, an optical disc, a magneto-optical disc, or a semiconductor memory.

In the personal computer 500 configured as mentioned above, the CPU 501 loads, for example, the program stored in the storage unit 508 on the RAM 503 via the input/output interface 505 and the bus 504, and executes the program. As a result, the above-mentioned sequence of processes is performed.

The program that is executed by the computer (CPU 501) can be recorded in the removable medium 511 and provided. The removable medium 511 is, for example, a package medium including a magnetic disc (including a flexible disc), an optical disc (a compact disc-read only memory (CD-ROM), a digital versatile disc (DVD), and the like), a magneto-optical disc, a semiconductor memory, or the like. Alternatively, the program can be provided through a wired or wireless transmission medium such as a local area network, the Internet, and digital satellite broadcasting.

In the computer, the program can be installed on the storage unit 508 via the input/output interface 505 when the removable medium 511 is mounted in the drive 510. Alternatively, the program can be received at the communication unit 509 via a wired or wireless transmission medium, and installed on the storage unit 508. Additionally, the program can be installed in advance on the ROM 502 or the storage unit 508.

Note that in the present specification, steps describing the above-mentioned sequence of processes obviously include, but are not limited to, processes that are performed in chronological order according to the described order, and may also include processes that are executed parallelly or individually.

In addition, the embodiments in the present disclosure are not limited to the above-mentioned embodiments, and can be variously changed in a range not departing from the gist of the present disclosure.

In addition, the configuration described above as a single device (or processing unit) may be divided and configured as a plurality of devices (or processing units). To the contrary, the configuration described above as a plurality of devices (or processing units) may be combined and configured as a single device (or processing unit). In addition, needless to say, a configuration other than the above-mentioned configuration may be added to the configuration of each device (or each processing unit). Furthermore, as long as the configuration and the operation of the system as a whole are substantially the same, a part of the configuration of a certain device (or processing unit) may be included in the configuration of another device (or another processing unit). In other words, the present technology is not limited to the above-mentioned embodiments, and can be variously changed in a range not departing from the gist of the present technology.

The preferable embodiments of the present disclosure have been described so far in detail with reference to the accompanying drawings. However, the disclosure is not limited to these examples. It is obvious that various types of variations or modifications can be conceived in a range of the technical idea described in the claims if a person has ordinary knowledge of the technical filed to which the present disclosure belongs. It is naturally understood that these variations or modifications also belong to the technical range of the present disclosure.

Note that the present technology can also be configured as follows.

(1) A surgical system including:
a surgical imaging device that captures an image for surgery; and
a surgical device including:
an image processing unit that processes the image captured by the surgical imaging device; and
a loading unit that reads, at time of startup, information of a program space on a memory recorded in a recording medium after startup of an operating system (OS) is finished, and loads the information of the program space on the memory.

(2) The surgical system according to (1), in which contents of the program space and an address for return are recorded in the recording medium as the information of the program space.

(3) The surgical system according to (1) or (2), in which the memory includes a double-data-rate (DDR) RAM.

(4) The surgical system according to any of (1) to (3), in which
the recording medium includes a solid state drive (SSD).

(5) The surgical system according to any of (1) to (4), further including
a recording unit that records the information of the program space in the recording medium after the startup of the OS is finished.

(6) The surgical system according to any of (1) to (5), in which
after the startup of the OS is finished, the recording unit starts up processes of a surgical application program, collaborates with a predetermined process of the processes, causes each process to reserve a resource and to execute sleep, and records the information of the program space.

(7) The surgical system according to any of (1) to (6), in which
order of starting up the surgical application program is order of proximity to hardware.

(8) The surgical system according to any of (1) to (7), in which
the surgical application program is an endoscopic surgical application program.

(9) The surgical system according to (8), in which
the surgical imaging device is an endoscope.

(10) The surgical system according to any of (1) to (7), in which
the surgical application program is a microscopic surgical application program.

(11) The surgical system according to (10), in which
the surgical imaging device is an endoscope.

(12) The surgical system according to any of (1) to (11), in which
the recording medium has a startup mode area indicating a startup mode,
the predetermined process changes a recording mode of the startup mode area of the recording medium to a high-speed startup mode when the information of the program space is recorded, and
in a case where the recording mode of the startup mode area of the recording medium is the high-speed startup mode, the loading unit reads the information of the program space recorded in the recording medium, and loads the information of the program space on the memory.

(13) A surgical method in which
a surgical device reads, at time of startup, information of a program space on a memory recorded in a recording medium after startup of an operating system (OS) is finished, and loads the information of the program space on the memory.

(14) A surgical device including
a loading unit that reads, at time of startup, information of a program space on a memory recorded in a recording medium after startup of an operating system (OS) is finished, and loads the information of the program space on the memory.

REFERENCE SIGNS LIST

1 Endoscopic surgical system
2 Camera head unit
5 CCU
9 Display device
22 CPU
51 Camera I/F unit
52 UI unit
53 DDR RAM
54 Image processing unit
55 Image output processing unit
56 SSD
100 Boot loader
101 Startup mode recording area
102 OS (Linux (registered trademark))
103 High-speed startup image area
104 Endoscope program area
105 User area
200 OS kernel
201 High-speed startup driver
202-1 to 202-n Various device drivers
203 Startup execution process
204 Endoscope application
205 User interface (UI) process
206 Image processing unit control process
207 Image output control process
208 Camera head control process
211 Endoscope program

The invention claimed is:

1. A medical system comprising:
a medical device including:
image processing circuitry configured to process the image captured by a medical imaging device;
loading circuitry configured to read, at time of startup, information of a program space on a memory recorded in a recording medium after startup of an operating system (OS) is finished and load the information of the program space on the memory; and
recording circuitry configured to record the information of the program space in the recording medium after the startup of the OS is finished,
wherein, after the startup of the OS is finished, the recording circuitry starts up processes of a medical application program, causes each process to reserve a resource and to execute sleep, and records the information of the program space.

2. The medical system according to claim 1, wherein contents of the program space and an address for return are recorded in the recording medium as the information of the program space.

3. The medical system according to claim 1, wherein the memory includes a double-data-rate (DDR) RAM.

4. The medical system according to claim 1, wherein the recording medium includes a solid state drive (SSD).

5. The medical system according to claim 1, wherein the recording circuitry is further configured to record the information of the processes of the medical application program is finished and the processes have executed said sleep.

6. The medical system according to claim 1, wherein order of starting up the medical application program is order of proximity to hardware.

7. The medical system according to claim 1, wherein the medical application program is an endoscopic medical application program.

8. The medical system according to claim 7, wherein the medical imaging device is an endoscope.

9. The medical system according to claim 1, wherein the medical application program is a microscopic medical application program.

10. The medical system according to claim 9, wherein the medical imaging device is a medical microscope.

11. The medical system according to claim 1, wherein the recording medium has a startup mode area indicating a startup mode,
the predetermined process changes a recording mode of the startup mode area of the recording medium to a high-speed startup mode when the information of the program space is recorded, and
in a case where the recording mode of the startup mode area of the recording medium is the high-speed startup mode, the circuitry reads the information of the program space recorded in the recording medium, and loads the information of the program space on the memory.

12. A medical method comprising:
reading, at time of startup, using circuitry of a medical device, information of a program space on a memory recorded in a recording medium after startup of an operating system (OS) and of processes of a medical application program is finished and the processes have executed sleep;
loading the information of the program space on the memory; and
recording the information of the program space in the recording medium after the startup of the OS is finished,
wherein, after the startup of the OS is finished, starting up processes of a medical application program, causing each process to reserve a resource and to execute sleep, and record the information of the program space.

13. A medical device comprising
circuitry configured to
read, at time of startup, information of a program space on a memory recorded in a recording medium after startup of an operating system (OS) and of processes of a medical application program is finished and the processes have executed sleep;
load the information of the program space on the memory; and
record the information of the program space in the recording medium after the startup of the OS is finished,
wherein, after the startup of the OS is finished, the circuitry starts up processes of a medical application program, causes each process to reserve a resource and to execute sleep, and records the information of the program space.

* * * * *